United States Patent [19]

Yamamoto et al.

[11] Patent Number: 4,751,907
[45] Date of Patent: Jun. 21, 1988

[54] AIR/FUEL RATIO DETECTING APPARATUS FOR INTERNAL COMBUSTION ENGINES

[75] Inventors: Tadahiro Yamamoto; Eiichi Ohnishi, both of Yokosuka; Tadaki Oota, Fujisawa; Hiroaki Oogane, Yokosuka; Minoru Osuga, Katsuta; Yoshishige Oyama, Katsuta, all of Japan

[73] Assignees: Nissan Motor Co., Ltd., Yokohama; Hitachi, Ltd., Tokyo, both of Japan

[21] Appl. No.: 906,949

[22] Filed: Sep. 15, 1986

[30] Foreign Application Priority Data

Sep. 27, 1985 [JP] Japan .................. 60-212488
Dec. 16, 1985 [JP] Japan .................. 60-280964

[51] Int. Cl.$^4$ .................. F02D 41/14; G01N 31/22
[52] U.S. Cl. .................. 123/489; 73/23; 123/589
[58] Field of Search .................. 123/440, 489, 589; 73/23; 364/431.05

[56] References Cited

U.S. PATENT DOCUMENTS 4,303,049 12/1981 Ikeura et al. .................. 123/440
4,391,130 7/1983 Nakano et al. .................. 123/489 X
4,502,444 3/1985 Rubbo et al. .................. 123/440

FOREIGN PATENT DOCUMENTS 57050 4/1983 Japan .

Primary Examiner—Tony M. Argenbright
Attorney, Agent, or Firm—Fay, Sharpe, Beall, Fagan, Minnich & McKee

[57] ABSTRACT

In an A/F ratio sensor of mixture supplied for an internal combustion engine, which has a detector for detecting the concentration of residual oxygen in exhaust gas and determines the A/F ratio by retrieving an air excess ratio table with an output of the detector, there is further provided an additional air introducing device, which introduces a predetermined quantity of air into the engine for a certain period of time, under the condition that the velocity of air flowing through a throttle valve is equal to the sonic velocity. The oxygen concentration detector is calibrated by the comparison of the outputs thereof before and after introduction of the additional air. According to this invention, the A/F ratio of the mixture can be detected accurately without the influence of the aged deterioration of the oxygen concentration.

16 Claims, 13 Drawing Sheets

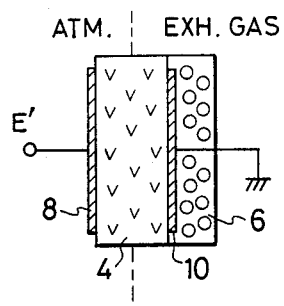
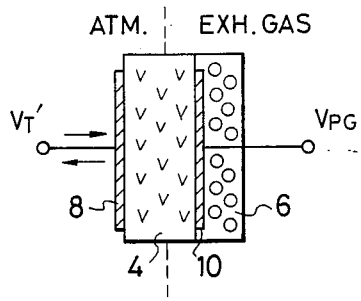
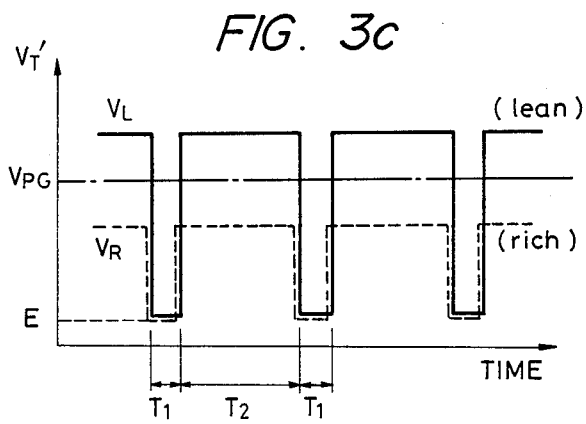
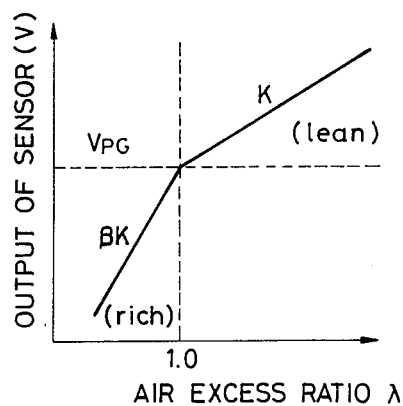
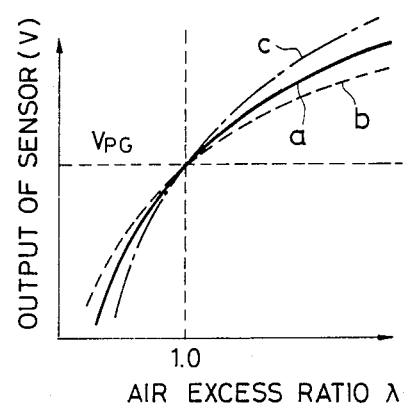

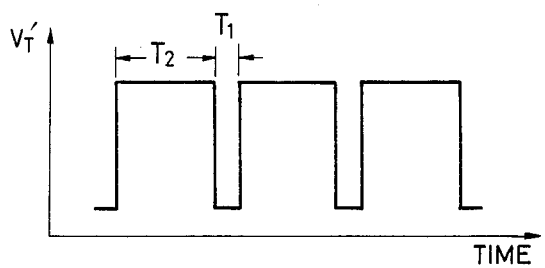
FIG. 13a
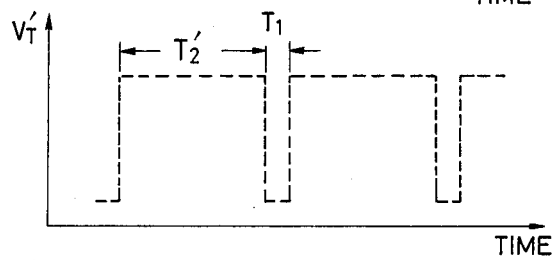
FIG. 13b
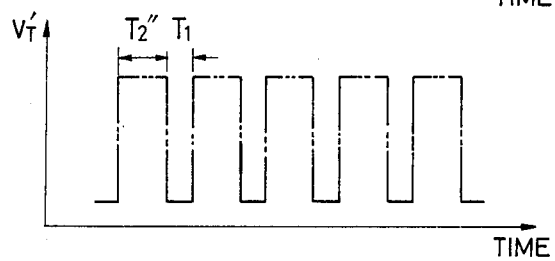
FIG. 13c
FIG. 14
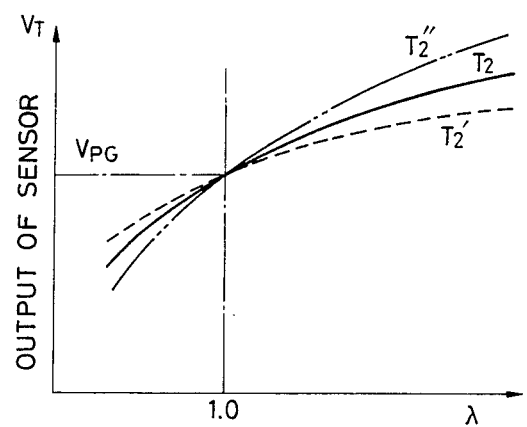

AIR/FUEL RATIO DETECTING APPARATUS FOR INTERNAL COMBUSTION ENGINES

BACKGROUND OF THE INVENTION

1. Field of The Invention

The present invention relates to an air/fuel ratio detecting apparatus for an internal combustion engine, which is capable of correcting the error in the measurement of the air/fuel ratio of a mixture supplied for the engine, which is caused by the aged deterioration resulted from the use extending over a long period of time.

2. Description of The Related Art

As is well known, the aged deterioration attends an air/fuel ratio detecting apparatus, which causes the error in the measurement of an air/fuel ratio of a mixture supplied for an internal combustion engine. To improve this, a calibrating method as disclosed in the Japanese Patent Laid-open Publication No. 58-57050 has been proposed, for example. According thereto, the error caused by the aged deterioration is corrected on the basis of an output signal produced by the air/fuel ratio detecting apparatus under the condition that an exhaust pipe, to which the detecting apparatus is attached, is filled with fresh air. However, it is very difficult to bring about such a condition in a short time. In the method of this prior art, unless fresh air perfectly fills the exhaust pipe, the output signal of the detecting apparatus becomes inappropriate for using it as a reference in calibrating the detecting apparatus. In addition, it is also not easy to confirm whether the exhaust pipe has been perfectly filled with fresh air.

SUMMARY OF THE INVENTION

An object of the present invention is to provide an air/fuel ratio detecting apparatus capable of easily correcting the error caused by the aged deterioration and accurately determining an air/fuel ratio of a mixture supplied for an engine.

A feature of the present invention is in that, in an apparatus for detecting an air/fuel ratio of a mixture which has means for detecting the concentration of residual oxygen in exhaust gas of an engine and determines the air/fuel ratio by retrieving an air excess ratio table prepared in advance with an output of the concentration detecting means, an additional air is introduced into the engine for a certain period of time during the steady state of operation of the engine, in addition to primary air sucked into the engine through an airflow meter and a throttle valve, and output signals which are obtained from the concentration detecting means before and after introduction of the additional air are processed, whereby the air/fuel ratio is determined in accordance with the processing result.

Other objects and features of this invention will become apparent upon reading the specification and inspection of the drawings and will be particularly pointed out in the claims.

BRIEF DESCRIPTION OF THE DRAWINGS

FIGS. 3a to 3c are explanatory drawings of the operation of the oxygen concentration detector shown in FIG. 1;

FIGS. 4a and 4b are diagrams showing example of an output characteritic of the oxygen concentration detector with respect to an air excess ratio;

FIGS. 13a to 13c and 14 are diagrams for explaining the operational principle of another embodiment of the present invention;

DESCRIPTION OF THE PREFERRED EMBODIMENTS

Before explanation of an embodiment of the present invention, the description will be made of an example of an air/fuel ratio detecting apparatus of the type to which the present invention is applied. However, it is to be noted that the type to which the present invention is applicable is not limited to that described in the following.

Figure 1:
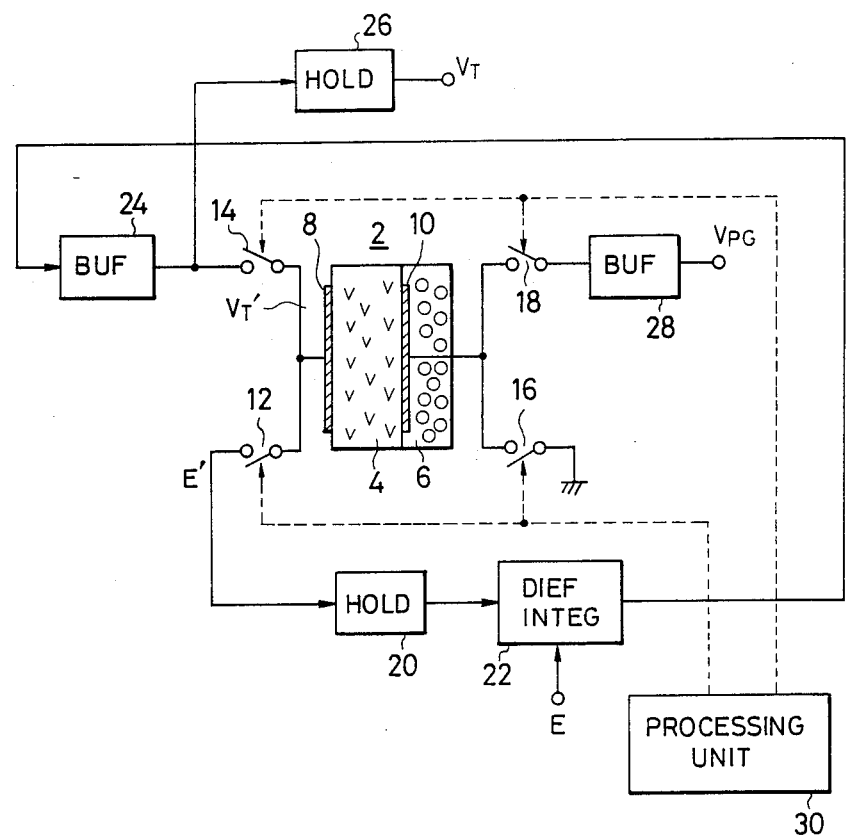
FIG. 1 is a schematic diagram showing the construction of a residual oxygen concentration detector used in the present invention.

Referring to FIG. 1, there is shown the arrangement of a residual oxygen concentration detector used in an air/fuel ratio detecting apparatus (called an A/F ratio sensor, hereinafter). As is well known, the concentration detector detects the concentration of residual oxygen remaining in exhaust gas from an internal combustion engine. An A/F ratio of a mixture supplied for the engine at that time is determined from the output value of the concentration detector.

In the figure, reference numeral 2 generally denotes a sensing portion of the concentration detector, which is shown in the simple form to facilitate the understanding of the principle of operation. The details thereof will be explained later with reference to FIG. 2. The sensing portion 2 comprises a solid electrolyte member 4 having the oxygen-ionic conductivity and a porous, diffusion-resistive layer 6 which comes into contact with the member 4. To one of surfaces of the member 4 attached is a first electrode 8, and this surface is exposed to the atmosphere. There is provided a second electrode 10 on the other surface of the member 4, which surface forms a boundary surface with the layer 6. Since, although described in detail later, exhaust gas from an internal combustion engine permeates into the porous layer 6, the other surface of the member 4 contacts with the exhaust gas.

To the first electrode 8, a pair of switches 12 and 14 are coupled, and similarly another pair of switches 16 and 18 are coupled to the second electrode 10. A hold circuit 20 is connected to the first electrode 8 through the switch 12, which receives the potential E' appearing at the first electrode 8 upon closure of the switch 12 and holds it even during opening of the switch 12. The potential E' is led to a differential integration circuit 22, in which the potential E' is compared with a reference E. The circuit 22 produces an output voltage in accordance with the difference between E and E', and the output voltage thereof is led to a buffer circuit 24. The circuit 24 applies the voltage according to the output from the circuit 22 to the electrode 8 when the switch 12 is opened and the switch 14 is closed. The output voltage of the buffer circuit 24 is also held by a hold circuit 26, the output voltage of which becomes an output signal $V_T$ of the concentration detector. The second electrode 10 is kept at the ground potential when the switch 16 is closed and, through a buffer circuit 28, at a constant ptential $V_{PG}$ when the switch 18 is closed.

Reference numeral 30 denotes a processing unit, which controls the switching operation of the switches 12 to 18 as well as the arithmetic logic operation for detecting a A/F ratio described in detail later. The processing unit 30 is formed by a usual microprocessor which is provided for the purpose of other various controls of an internal combustion engine such as a fuel injection control, an ignition timing control and so on. The control of the aforesaid switching operation is executed as a part of functions such a microprocessor has. Under the control of the processing unit 30, the switches 12, 16 are simultaneously opened or closed, and the switches 14, 18 are also operated simultaneously, but alternately with the switches 12, 16.

Figure 2:
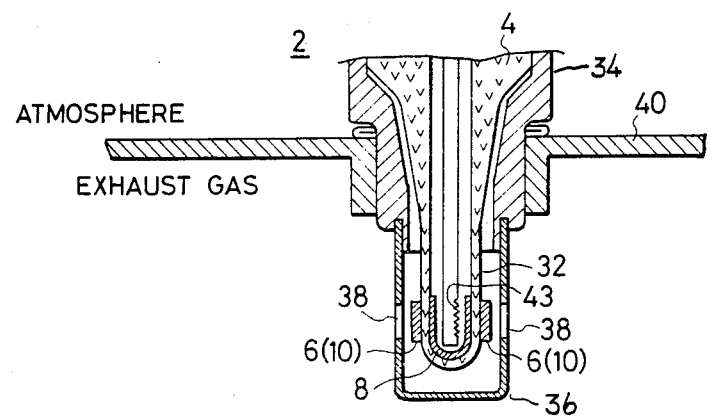
FIG. 2 shows a detailed structure of a part of a sensing portion of the oxygen concentration detector shown in FIG. 1.

The detailed structure of a main part of the sensing portion 2 is shown in FIG. 2, in which like reference numerals indicate the same parts as in FIG. 1. The solid electrolyte member 4 is made hollow and has a cylindrical portion 32 at its top portion, one end of which is closed. To the inner surface of the closed top portion, the first electrode 8 is attached. Fresh air is introduced into the hollow portion of the member 4 from the atmosphere. Although a wiring connects the electrode 8 with an external circuit, it is omitted for simplification of the drawing. The diffusion-resistive layer 6 is provided on the outer surface of the cylindrical portion 32 and in the vicinity of the location of the first electrode 8. The second electrode 10 is attached to the outer surface of the cylindrical portion 32 so as to be covered by the layer 6. A wiring also connects the electrode 10 to the external circuit, however it is omitted in the drawing.

The solid electrolyte member 4 as a whole is covered and supported by an appropriate supporting member 34, except the cylindrical portion 32 thereof. The cylindrical portion 32 is surrounded by a protection member 36, in a part of which there are provided holes 38. The thus constructed sensing portion 2 is attached to an exhaust pipe of an internal combustion engine in such a manner that the portion 32 surrounded by the protection member 36 is positioned within the exhaust pipe through a wall 40 thereof. With this structure, exhaust gas within the exhaust pipe enters into a chamber surrounded by the member 36 through the holes 38, so that the diffusion-resistive layer 6 is exposed to the exhaust gas. Further, during operation, the vicinity of the electrodes 8 and 10 are heated about 750° C. by a heater 43.

Referring next to FIGS. 3a to 3c, the explanation will be done of the operation of the residual oxygen concentration detector mentioned above. At first, the switches 12, 16 are closed and the switches 14, 18 are opened, in response to signals from the processing unit 30. FIG. 3a outlines the circuit situation of this time. In this case, since the electrode 10 is grounded, there appears the potential E' at the electrode 8, which is in proportion to the difference in the partial pressure of oxygen between the atmosphere and the exhaust gas. The potential E' is held by the hold circuit 20, and compared with the reference E in the differential integration circuit 22. The circuit 22 produces the output voltage in accordance with the difference between E and E'. For the convenience' sake, the operation in this situation is called a first mode of operation, hereinafter.

Next, the switches 12, 16 are opened and the switches 14, 18 are closed, in response to the signals from the processing unit 30. FIG. 3b outlines the circuit situation of this time. In this case, the electrode 10 is maintained at the constant voltage $V_{PG}$, and the voltage $V_T$ which is proportional to the output of the circuit 22 is applied to the electrode 8. If, therefore, the voltage $V_T$ is higher than the voltage $V_{PG}$, current flows through the solid electrolyte member 4 in the direction as shown by a rightward arrow, whereby oxygen within the exhaust gas is extracted to the atmosphere. If the voltage $V_T$ is lower than the voltage $V_{PG}$, current flows through the member 4 in the direction as shown by a leftward arrow, whereby oxygen is introduced into the exhaust gas from the atmosphere. The operation in this case is called a second mode of operation.

By the way, the voltage $V_T$ is determined by the difference between the reference E and the potential E' measured in the first mode. Therefore, the voltage $V_{T'}$ is so controlled that the potential E' becomes equal to the reference E. This fact means that the partial pressure of oxygen in the vicinity of the electrode 10 is maintained at the value corresponding to the reference E. Practically, the reference E is set about 0.4 volts. The selection of this potential means that the partial pressure of oxygen in the vicinity of the electrode 10 is maintained at $10^{-12}$ atms, at which partial pressure the concentration of oxygen molecules in the exhaust gas is almost zero. Therefore, the voltage $V_T$ is in proportion to the concentration of oxygen included in the exhaust gas which permeated into the porus layer 6. This voltage $V_T$ is held by the hold circuit 26 and output therefrom as a concentration signal $V_T$.

FIG. 3c is a chart showing the operation as mentioned above with respect to time. Namely, for a period $T_1$, the first mode of operation is conducted, and after that, the second mode of operation is executed for a period $T_2$. If a mixture burnt in an internal combustion engine is lean, the concentration of residual oxygen in the exhaust gas is high and the difference in the partial pressure of oxygen between the atmosphere and the exhaust gas becomes small. Therefore, the the potential $E'$ measured in the first mode becomes low, so that the difference between E and $E'$ becomes large and the higher voltage $V_L$ is applied to the elctrode 8 as $V_T'$ in the second mode. On the contrary, when the mixture is rich, the concentration of oxygen in the exhaust gas is low and the the potential $E'$ becomes high, so that the difference between E and $E'$ becomes small and the lower voltage $V_R$ is applied to the electrode 8 as $V_T'$ in the second mode.

FIG. 4a is a graph showing an output characteristic of the residual oxygen concentration detector as mentioned above, in which the ordinate indicates the output voltage $V_T$ of the detector and the abscissa an air excess ratio $\lambda$. As is well known, the air excess ratio $\lambda$ is represented as a ratio of an actual A/F ratio to the stoichiometric value (14.7). Therefore, $\lambda = 1.0$ means that the actual A/F ratio is equal to the stoichiometric value. Exhaust gas from an internal combustion engine operating under the stoichiometric A/F ratio does not include any residual oxygen because of the complete combustion of the mixture in the engine. As a result, the partial pressure of oxygen in the vicinity of the electrode 10 becomes equal to $10^{-12}$ atms, and therefore the potential $E'$ is equal to the reference E (0.4 volts), so that the output voltage $V_T$ also becomes equal to the constant voltage $V_{PG}$.

In the region of $\lambda > 1.0$ (lean mixture), the partial pressure of oxygen becomes high because of excess residual oxygen in the exhaust gas, and the output voltage $V_T$ increases with the concentration of the residual oxygen. In the region of $\lambda < 1.0$ (rich mixture), the output voltage $V_T$ of the oxygen concentration detector is dominated by combustible components remaining in the exhaust gas. The components consist mainly of CO, $H_2$ and HC. Since diffusion coefficients of those components in the diffusion-resistive layer 6 are different from that of oxygen, a gain $\beta K$ of the concentration detector in this region is different from that K in the region of $\lambda > 1.0$.

In FIG. 4a, the output characteristic is shown as if it varies linearly in the respective regions, however the actual characteristic becomes nonlinear as shown by a curve a in FIG. 4b, because the resistivity depends largely on the position within the diffusion-resistive layer 6. Further, in the case where the porosities of the porous layer 6 have been choked up due to the use for a long time, the output characteristic changes as shown by a curve b (a broken line). On the other hand, in the case where a part of the layer 6 has peeled off, the output characteristic changes as shown by a curve c (a chain line).

In this way, the output characteristic changes due to the aged deterioration of the sensing portion 2. As will be understood from FIG. 4b, however, the point of the output voltage $V_{PG}$, at which point $\lambda$ is 1.0, never changes, even though the sensing portion 2 has suffered the aged deterioration as mentioned above. This is because the partial pressure of oxygen in the vicinity of the electrode 10 is controlled so as to be always equal to that in the case of the stoichiometric A/F ratio. Namely, the transfer of oxygen between the atmosphere and the exhaust gas does not occur at $\lambda = 1.0$, and therefore no current flows through the solid electrolyte member 4, so that $V_T$ is maintained at $V_{PG}$.

In the residual oxygen concentration detector shown in FIG. 1, the single sensing portion 2 is used, switched for the common use in both the first mode and the second mode of operation. If the sensing portion comprises two sets of solid electrolyte members each having a pair of electrodes and the respective sets are used exclusively for the respective modes of operation, the circuit arrangement accompanying the sensing portion becomes more simpler.

Figure 5:
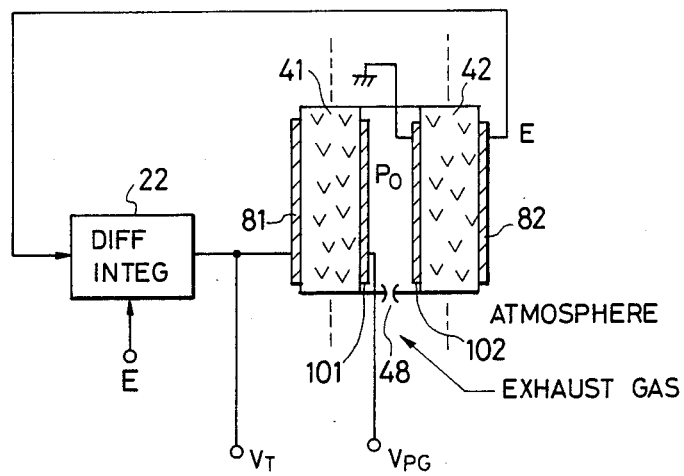
FIG. 5 is a schematic diagram showing the construction of a residual oxygen concentration detector of another type, which can be also used in the present invention.

A residual oxygen concentration detector of such a type is shown in FIG. 5, in which like references denote the same parts as in FIG. 1. In this detector, there are provided two solid electrolyte members 41 and 42, to which a pair of electrodes 81, 101 and 82, 102 are attached respectively. Two sets of the thus constructed sensing units defines a chamber, which has a small hole 48 and into which exhaust gas is introduced through the hole 48. Accordingly, surfaces of the members 41, 42, on which the electrodes 101, 102 are attached, are exposed to the exhaust gas. The reverse surfaces of the members 41, 42 are exposed to the atmosphere. With this structure, the partial pressure $P_0$ of oxygen in the exhaust gas introduced into the chamber can be detected in the same manner as the detector shown in FIG. 1. The output characteristic becomes the same as that shown in FIG. 4a or 4b. Therefore, an A/F ratio sensor of the present invention can be also realized by utilizing this type of the residual oxygen concentration detector.

The two types of the detector described above both were a detector which can measure the oxygen concentration in both the regions of $\lambda < 1.0$ and $\lambda > 1.0$. However, the present invention is applicable to a so called lean sensor, which is also often used and can measure the oxygen concentration only in the region that $\lambda$ is equal to or larger than 1.0.

Figure 6:
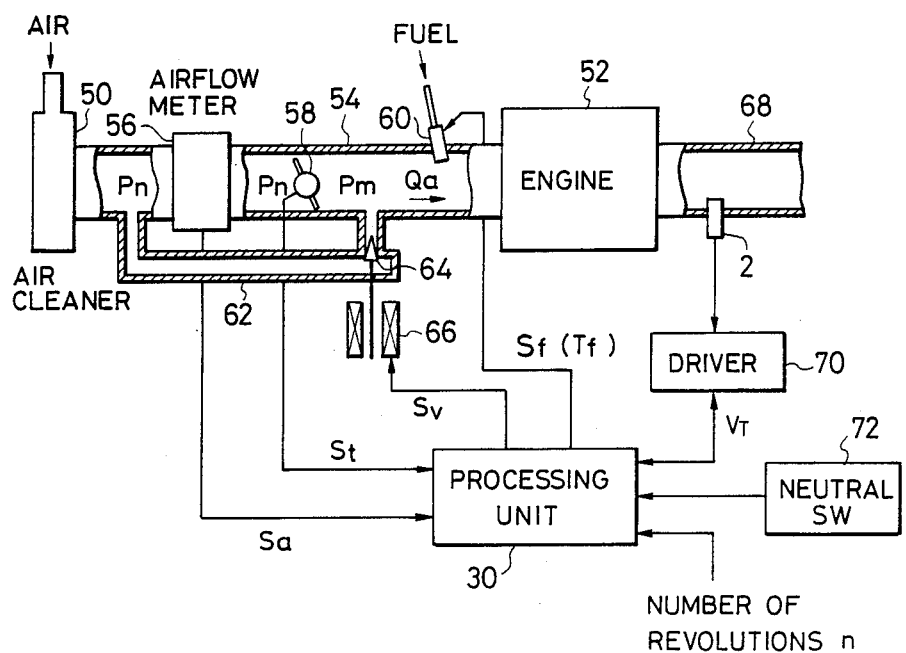
FIG. 6 schematically shows the arrangement of an air/fuel ratio detecting apparatus according to an embodiment of the present invention.

Referring now to FIG. 6, the description will be made of an A/F ratio sensor according to an embodiment of the present invention.

In FIG. 6, reference numeral 50 denotes an air cleaner, which is coupled to an engine 52 by a suction pipe 54. The suction pipe 54 is provided with an airflow meter 56, a throttle valve 58 and a fuel injector 60 in the order as shown in the figure. Bridging the airflow meter 56 and the throttle valve 58, there is provided a by-pass passage 62, through which additional air is introduced into the engine 52. The passage 62 has a solenoid nozzle 64 at its outlet end, which is actuated by a solenoid coil 66 and controls the communication of the additional air flowing therethrough.

The airflow meter 56 measures the quantity of primary air flowing therethrough and produces an output signal $S_a$ to the processing unit 30. In this embodiment, an airflow sensor of the hot wire type has been employed, however other types of the airflow meter such as a vane type or an intake manifold pressure type can be also utilized. To the throttle valve 58 attached is a throttle switch (not shown), which produces an output signal $S_t$ to the processing unit 30 when the throttle valve 58 is closed. Receiving the signals $S_a$ and $S_t$ as well as some other signals as described later, the processing unit 30 executes the predetermined processing, and produces a fuel injection control signal $S_f$ to the fuel injector 60 and a nozzle control signal $S_v$ to the solenoid coil 66. The nozzle 64, when it is opened, introduces additional air for the calibrating operation described later into the engine 52 for a predetermined period. The method of introducing such an additional air can be substituted, for example, by opening the throttle valve 58 by a certain angle for the predetermined period. The fuel injection control signal $S_f$ is a signal of the valve opening time $T_f$ (injection time), during which a valve of the fuel injector 60 is opened and the fuel is injected into the sucked air.

Reference numeral 68 denotes an exhaust pipe, to which the sensing portion 2 of the oxygen concentration detector is attached in the manner as already described. Reference numeral 70 denotes a driver circuit of the detector, which includes all components of the arrangement of FIG. 1 or FIG. 5, except the sensing portion 2. Namely, both the sensing portion 2 and the driver circuit 70 forms the oxygen concentration detector as shown in those figures. Therefore, the concentration signal $V_T$ for determining the A/F ratio is output from the driver circuit 70. This signal $V_T$ is led to the processing unit 30. To the processing unit 30 is also applied a signal from a neutral switch 72 which is furnished to a transmission (not shown). This signal means that the transmission is in the neutral position. Another signal to the processing unit 30 is a signal representative of the number n of revolutions of the engine 52.

In the following will be explained the operation of this embodiment. In the arrangement shown in the figure, a so called basic injection time is calculated on the basis of the the signal $S_a$ from the airflow meter 56 and the number n of revolutions of the engine 52. The basic injection time is corrected by various signals, for example, the A/F ratio signal $V_T$, a temperature of the engine 52 and other signals needed for the required control performance, although all of them are not shown. The injection time $T_f$ is obtained by this correcting operation. These operations can be executed in the processing unit 30 in accordance with various kinds of known algorithm. Further, since the way of obtaining the injection time $T_f$ has nothing to do with the present invention and, contrary speaking, the present invention is not limited to any particular method of determining the injection time $T_f$, there is omitted here further description of the manner of obtaining the injection time $T_f$.

Now, a first stage of the operation characterized by this embodiment is executed under the operational condition of the engine 52 that the velocity of the primary air flowing through the throttle valve 58 is equal to the sonic velocity. Such a condition is created, when the throttle valve 58 is at the idle angle and the engine 52 is idling. Further, under such a condition, the relation $P_n >> P_m$ is established, wherein $P_n$ is a pressure within the suction pipe 54 on the upstream side of the throttle valve 58 and $P_m$ a pressure on the downstream side thereof. The diameter of the outlet of the nozzle 64 is so selected that the aforesaid relation in pressure is not destroyed even when the additional air is introduced into the downstream of the throttle valve 58 through the nozzle 64. If the above mentioned relation in pressure is always satisfied, the quantity of the primary air flowing through the airflow meter 56 does not change even though the additioal air is introduced through the nozzle 64, and therefore the signal $S_a$ does not change, either.

In this manner, if the velocity of the additional air flowing through the nozzle 64 is equal to the sonic velocity, the quantity $\Delta Q_a$ of the air introduced through the by-pass passage 62 is expressed by the following formula:

$$\Delta Q_a = a \sqrt{\gamma \left(\frac{2}{\gamma+1}\right)^{\frac{\gamma+1}{\gamma-1}} P_0 \rho} \quad (1)$$

wherein a represents the opening area of the nozzle 64, $\gamma$ the specific heat ratio, and $\rho$ the density of the air (depending on the temperature). As apparent from the formula (1), the quantity $\Delta Q_a$ can be accurately obtained as a function of the opening area a of the nozzle 64 only, if the pressure $P_n$ and the temperature (hence the density) are almost constant. Further, if the correction is conducted by the pressure $P_n$ and the temperature, the more accurate $\Delta Q_a$ can be determined, even though they have varied.

Now assuming that during closure of the nozzle 64 the quantity of the primary air measured by the airflow meter 56 is $Q_{a0}$. Then, the fuel injection is conducted for the time $T_{f0}$, and the quantity of fuel injected becomes $Q_{f0}$ ($=Q_{a0}/n$). Further, assuming that the nozzle 64 is opened at time point t1, the additional air of the quantity $\Delta Q_a$ is introduced into the downstream of the throttle valve 58, and the nozzle 64 is closed at time point t2. In this case, as already described, the quantity of the primary air flowing through the airflow meter 56 does not change and equals $Q_{a0}$. Therefore, the quantity $Q_{f0}$ of fuel to be injected, which is calculated on the basis of $Q_{a0}$, does not change, and as a result, the A/F ratio of the mixture supplied for the engine 52 changes. The change in the A/F ratio by opening of the nozzle 64 becomes as follows:

| (before opening) | (after opening) |
|---|---|
| $Q_{a0}/Q_{f0}$ | $(Q_{a0} + \Delta Q_a)Q_{f0}$ |

Figure 7:
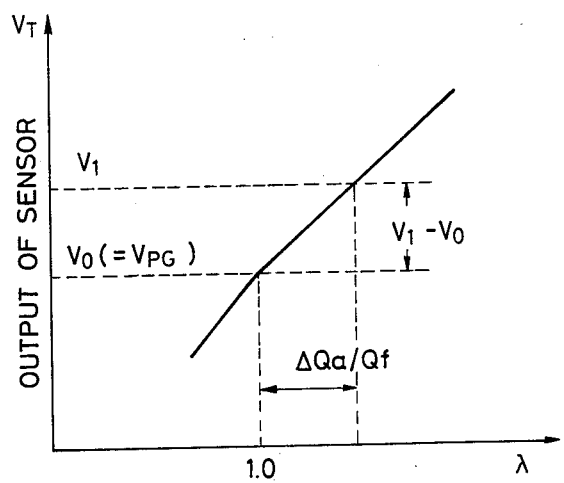
FIGS. 7 and 8(a–e) are drawings for explaining the operational principle of the embodiment shown in FIG. 6.

In the present invention, the aged deterioration of the residual oxygen concentration detector is detected by learning the difference in the A/F ratios before and after opening of the nozzle 64. Referring next to FIG. 7, the description will be made of the principle of the method of detecting the aged deterioration. This detecting operation is executed while engine 52 operates under the condition of $\lambda = 1.0$. Such an operational condition of the engine 52 can be brought about by the feedback control, by which the output voltage $V_T$ of the concentration detector is made equal to the voltage $V_{PG}$. This is for the purpose of utilizing the fact that the output voltage of the concentration detector never changes at the point $\lambda = 1.0$ in spite of the aged deterioration. By fixing this point, the quantity $Q_f$ of fuel injected during the detecting operation can be made known.

Under these conditions, the output voltage $V_0$ of the residual oxygen concentration detector during closure of the nozzle 64 is represented as follows:

$$V_0 = K \, Q_{a0}/Q_{f0} \quad (2)$$

wherein K is a gain of the oxygen concentration detector. Further, the output voltage $V_1$ of the oxygen concentration detector upon opening of the nozzle 64 is represented by the following formula.

$$V_1 = K(Q_{a0} + \Delta Q_a)/Q_{f0} \quad (3)$$

The difference between both the output voltages $V_0$ and $V_1$ becomes as follows.

$$V_1 - V_0 = K\Delta Q_a/Q_{f0} \quad (4)$$

Namely, the change in $\lambda$ caused by opening of the nozzle 64 is $\Delta Q_a/Q_{f0}$, and the change in the output voltage of the oxygen concentration detector in response thereto becomes $V_1 - V_0$. This is illustrated in FIG. 7. Further, the above formula (4) is reformed as follows.

$$K = (V_1 - V_0)Q_{f0}/\Delta Q_a \quad (5)$$

Since $\Delta Q_a$ can be obtained from the formula (1) and also $Q_{f0}$ is known as already mentioned, the gain K can be specified from the above formula (5). The thus obtained gain K is a gain of the oxygen concentration detector at the present time, and since the aged deterioration appears in the form of the change in the gain of the detector, the detected present gain K is compared with an original gain in order to learn the aged deterioration of the detector.

Figure 8:
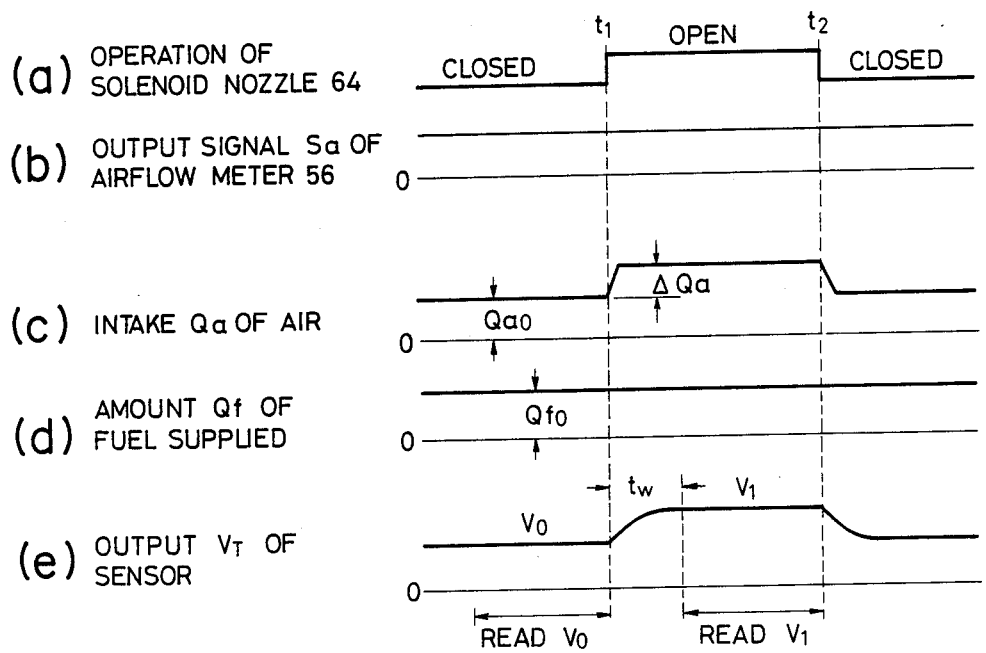

FIG. 8 is a time chart showing the change of the signals or variables in the various parts and the timing of taking data into the processing unit 30. At first, the output voltage $V_0$ of the oxygen concentration detector is read into the processing unit 30, while the nozzle 64 is closed (cf. FIG. 8(e)). At the time point $t_1$ the nozzle 64 is opened (cf. FIG. 8(a)). Although, even upon opening of the nozzle 64, the output signal $S_a$ of the airflow meter 56 and hence the quantity $Q_f$ of the fuel supplied for the engine 52 do not change (cf. FIGS. 8(b) and (d)), the intake $Q_a$ sucked into the engine 52 increases by $\Delta Q_a$ from $Q_{a0}$ (cf. FIG. 8(c)). At time $t_w$ after opening of the nozzle 64, the output voltage $V_1$ of the detector is read into the processing unit 30 (cf. FIG. 8(e)). The time $t_w$ is selected to be the duration sufficient for airflow to become stable after the nozzle 64 is opened. After having read the voltage $V_1$, the nozzle 64 is closed again at the time point $t_2$ (cf. FIG. 8(a)).

Figure 9:
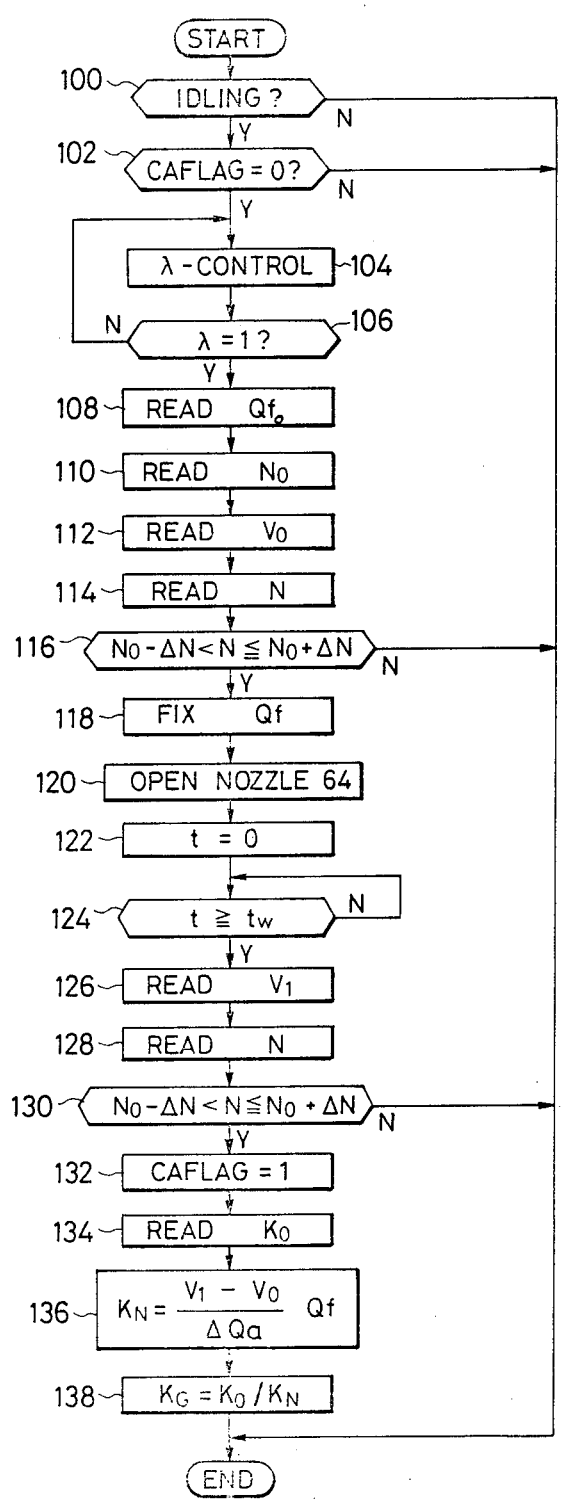
FIG. 9 is a flow chart showing a part of the operation of the embodiment of FIG. 6, in which the operation until obtaining a correcting factor $K_G$ is illustrated.

The above described control of the nozzle 64 and the arithmetic logic operation for learning the deterioration of the oxygen concentration detector are executed by the processing unit 30. The operation of the processing unit 30 will be explained, referring to a flow chart shown in FIG. 9. Further, the operation shown in FIG. 9 is called a calibrating operation, hereinafter, because in this operation the deterioration of the oxygen concentration detector and the degree thereof are detected and a correcting factor is found.

After start, it is discriminated at step 100 whether or not the engine 52 is in the condition of idling. This discrimination is performed on the basis of the signal from the neutral switch 72 and the number of revolutions of the engine 52. If the engine 52 is in the idling condition, the operation goes to step 102, and otherwise it is ended. At step 102, it is searched whether or not a flag CAFLAG for the calibrating operation is zero. This is the flag which is raised when all data necessary for the calibrating operation have been read. When the flag CAFLAG is zero, the operation goes to step 104, and otherwise it is ended because the calibrating operation has been finished.

By repeating steps 104 and 106, the engine 52 falls into the operational condition of $\lambda = 1.0$. Under such operational condition of the engine 52, the quantity $Q_{f0}$ of the fuel supplied at that time, the number $N_0$ of revolutions of the engine 52, and the output voltage $V_0$ of the oxygen concentration detector are read successively (steps 108, 110 and 112). At step 114, the number N of revolutions is read again, and it is checked at step 116 whether or not the change in the number N of revolutions remains within a predetermined range. This step is for the purpose of confirming that the operational condition of the engine 52 does not change from that at the time of the preceding steps, at which data necessary for the calibrating operation have been taken. If the operational condition changes, data read at the respective steps becomes invalid and therefore the further operation is stopped. If there is no change in the operationa condition, the operation proceeds to step 118.

At step 118, the quantity $Q_f$ of the fuel to be injected is fixed at the value $Q_{f0}$ read at step 108. After that, the nozzle 64 is opened at step 120. The operation of steps 122 and 124 is a timer operation. Therefore, after the time $t_w$ from opening of the nozzle 64, steps 126 and 128 are executed successively, by which the output voltage $V_1$ of the oxygen concentration detector and the number N of revolutions are read. At step 130, the number N of revolutions of the engine 52 is checked again. This step has the same purpose as step 116. If the number N of revolutions changes, the operation is ended. In the case where the change in the number N of revolutions remains within the predetermined range, the value 1 is set in the flag CAFLAG at step 132, which means that reading of data necessary for the calibrating operation has been finished.

After having taken necessary data into the processing unit 30, an old gain $K_O$, which has been obtained and stored in the last calibrating operation, is read out from the storage at step 134. At step 136, a new gain $K_N$ is calculated in accordance with the formula (5) on the basis of data read in the foregoing steps. Next, a ratio $K_G$ between $K_O$ and $K_N$ is calculated at step 138. The ratio $K_G$ is called a correcting factor hereinafter. If the thus otained correcting factor $K_G$ is not 1, i.e., if the new gain $K_N$ does not equal the old one $K_O$, that fact means that the oxygen concentration detector deteriorates. If the deterioration, e.g., the choking-up of the porous layer 6, is severe, the value of the new gain $K_N$ becomes smaller than the old one $K_O$ in accordance with the degree of the deterioration and therefore the factor $K_G$ becomes a value different from 1 in response thereto. Namely, the factor $K_G$ can be said to indicate the degree of the deterioration of the detector. Therefore, the factor $K_G$ is available to correct the A/F ratio determined on the basis of the value measured by a deteriorated detector.

Figure 10:
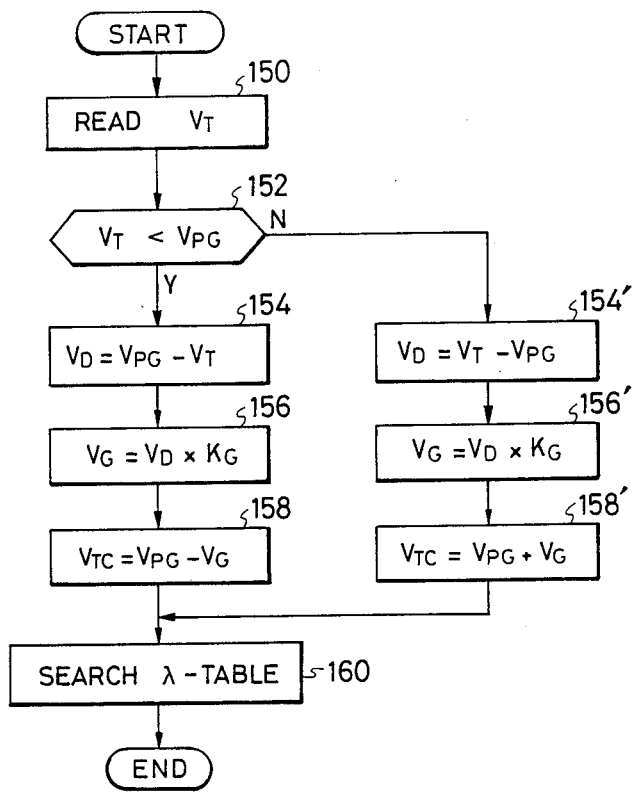
FIG. 10 is a flow chart showing another part of the operation of the embodiment of FIG. 6, in which there is illustrated the operation of correcting an output of the oxygen concentration detector by using the correcting factor $K_G$.

Referring next to FIG. 10, the description will be made of the operation of the correction of the incorrectly measured value and the determination of the correct A/F ratio.

By the way, taking the case where the porosities of the porous layer 6 have been choked up (cf. the broken line b in FIG. 4b) as an example, the actually measured voltage indicates the value lower than the normal value (the solid line a in the same figure) in the range of $\lambda > 1.0$ and the former is higher than the latter in the range of $\lambda < 1.0$. Further, if a part of the layer 6 has peeled off, the relation of the output voltage of the detector versus $\lambda$ as mentioned above becomes contrary. Therefore, the correcting operation must be separately conducted on the respective ranges of $\lambda < 1.0$ and $\lambda > 1.0$.

First of all, the output voltage $V_T$ of the oxygen concentration detector at that time is read at step 150, and at step 152 the output voltage $V_T$ is compared with the voltage $V_{PG}$ which is the output voltage when $\lambda$ is 1.0. When $V_T$ is smaller than $V_{PG}$, i.e., in the range of $\lambda<1.0$, the operation goes to step 154, at which a difference $V_D$ is obtained by subtracting $V_T$ from $V_{PG}$. At step 156, a correction value $V_G$ is obtained by multiplying the difference $V_D$ by the correcting factor $K_G$ which is already obtained by the operation of FIG. 9. Further, a corrected $V_{TC}$ is obtained by subtracting $V_G$ from $V_{PG}$ at step 158. Returning to step 152, when $V_T$ is larger than $V_{PG}$, i.e., in the range of $\lambda>1.0$, the operation goes to step 154'. In the process starting with step 154', there is taken place the similar operation to the process of steps 154 to 158, however the difference $V_D$ is obtained by subtracting $V_{PG}$ from $V_T$ and the corrected $V_{TC}$ is obtained by adding $V_G$ to $V_{PG}$. In accordance with the thus corrected $V_{TC}$, at step 160 an air excess ratio table ($\lambda$-table), which is described in detail below, is searched. Thereby the correct A/F ratio is identified and utilized for the accurate fuel injection control.

Figure 11:
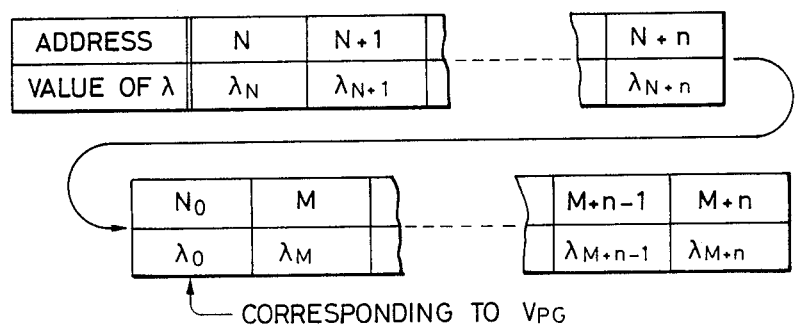
FIG. 11 is a drawing for explaining an example of an air excess ratio table.

FIG. 11 shows an example of the $\lambda$-table. The table is prepared within the storage in the processing unit 30 and has addresses corresponding to the output voltage $V_T$ of the oxygen concentration detector. In the example shown, addresses N, N+1, ..., N+n are assigned to the output voltage $V_T$ in the range of $\lambda<1.0$ and addresses M, ..., M+n−1, M+n are assigned to the output voltage $V_T$ in the range of $\lambda>1.0$. Further, an address corresponding to the voltage $V_{PG}$ ($\lambda=1.0$) is $N_0$. In the storage locations of the respective addresses, the corresponding $\lambda$s are stored. If the stored $\lambda$s are the correct values, which have been determined in advance on the basis of the normal output voltages of an undeteriorated oxygen concentration detector, the value of $\lambda$ read out in response to the corrected $V_{TC}$ indicates the correct one.

In the above described embodiment, the correcting operation of FIG. 10 was executed every time the output voltage of the oxygen concentration detector is read into the processing unit 30. However, the desired purpose or effect of the present invention can be also achieved by rewriting the contents of the $\lambda$-table shown in FIG. 11 after the correcting factor $K_G$ has been once obtained by the calibrating operation of FIG. 9. In the following, the description will be made of the method of rewriting the contents of the $\lambda$-table, referring to FIG. 12.

First of all, at step 162, a reciprocal value $K_{G'}$ of the correcting factor $K_G$ is calculated. Next, at step 164, the value of $\lambda$ stored at the address N of the $\lambda$-table is read out. In the process from step 166 to step 170, the corrected $V_{TC}$ is obtained in the similar way to the corresponding process in the flow chart of FIG. 10. At step 172, the value of $\lambda$, which has been read out at step 164, is stored into the address of the $\lambda$-table corresponding to the corrected $V_{TC}$. Namely, the content of the address corresponding to the corrected $V_{TC}$ is rewritten by the value of $\lambda$, which has been read out at step 164. After that, the address value N is increased by 1 at step 174, and it is discriminated at step 176 whether or not the address value N has reached N+n. If not, the operation returns to step 164, and the above mentioned process is repeated until the address value N becomes N+n. When the address value N has reached N+n, the operation goes to step 178. The aforesaid flow from step 164 to step 176 is the process for rewriting the contents stored in the addresses N to N+n of the $\lambda$-table. Namely, the scope of $\lambda<1.0$ of the $\lambda$-table is rewritten by this process.

Succeeding to step 176, step 178 is executed, at which the value of $\lambda$ stored at the address M of the $\lambda$-table is read out. In the process from step 180 to step 184, the corrected $V_{TC}$ is obtained in the similar way to the corresponding process in the flow chart of FIG. 10. At step 186, the value of $\lambda$, which has been read out at step 178, is stored into the address of the $\lambda$-table corresponding to the corrected $V_{TC}$, which has been obtained at step 184. That is, the content of the address corresponding to the corrected $V_{TC}$ is rewritten by the value of $\lambda$, which has been read out at step 178. Thereafter, the address value M is increased by 1 at step 188, and it is discriminated at step 190 whether or not the address value m has reached M+n. If not, the operation returns to step 178, and the process from step 178 to step 188 is repeated until the address value M becomes equal to M+n. When the address value M has reached M+n, the operation ends. By this process starting with step 178 the contents stored in the addresses M to M+n of the $\lambda$-table are rewritten. Namely, the scope of $\lambda>1.0$ of the $\lambda$-table can be rewritten.

In this way, once the $\lambda$-table has been corrected in accordance with the degree of deterioration of the oxygen concentration detector, the value of $\lambda$ read out from the $\lambda$-table can be immediately utilized for the subsequent fuel injection control.

In the foregoing embodiments, the correction of the output voltage of the oxygen concentration detector has been carried out by using the correcting factor $K_G$ or its reciprocal value $K_{G'}$ obtained on the basis of the old gain $K_O$ and the new gain $K_N$ of the detector, and the value of $\lambda$ to be used for the fuel injection control is specified on the basis of the corrected voltage $V_{TC}$. In the following the description will be made of another embodiment, in which the gain itself of the oxygen concentration detector is corrected in accordance with the degree of the deterioration thereof.

Referring at first to FIGS. 13 and 14, the operational principle of the another embodiment will be explained. This embodiment utilizes the fact that the output voltage $V_T'$ with respect to the same value of $\lambda$ can be changed by altering the ON-OFF period of the signal to the switches 12 to 18 shown in FIG. 1, i.e., by changing the time duration of applying $V_T'$ to the electrode 8. Namely, the gain of the oxygen concentration detector varies in accordance with the ON-OFF period of the signal to the switches 12 to 18. FIG. 13a shows the standard relation between the time periods $T_1$ and $T_2$. In the same manner as in FIG. 3c, the switches 12, 16 are closed and the switches 14, 18 are opened for the time period $T_1$ (the first mode of operation) and, on the contrary, the switches 12, 16 are opened and the switches 14, 18 are closed for the time period $T_2$ (the second mode of operation).

If the time period $T_2$ for the second mode of operation is changed to $T_2'$ which is longer than $T_2$, as shown in FIG. 13b, the gain of the oxygen concentration detector becomes small, as shown by a broken line in FIG. 14. This is because, if the time period of the second mode of operation is extended, the sufficient amount of oxygen can be transferred through the solid electrolyte member 4 between the atmosphere and the exhaust gas even with the small amount of current flowing through the member 4. On the contrary, if the time period $T_2$ of the second mode of operation is shortened to $T_2''$, as shown in FIG. 13c, the gain of the detector becomes large, as shown by a chain line in FIG. 14. The reason therefor is as follows. When the time period of the second mode of operation is shortened, the current flowing through the member 4 is increased and the sufficient amount of oxygen transfer must be ensured in order to maintain the potential of the electrode 8 at 0.4 volts. Further, as will be understood from FIGS. 13a to 13c, the time period $T_1$ of the first mode of operation is not changed.

Moreover, it is to be noted that, as already described, the output voltage of the oxygen concentration detector is kept at $V_{PG}$ in any cases described above, when $\lambda$ is 1.0.

Figure 15:
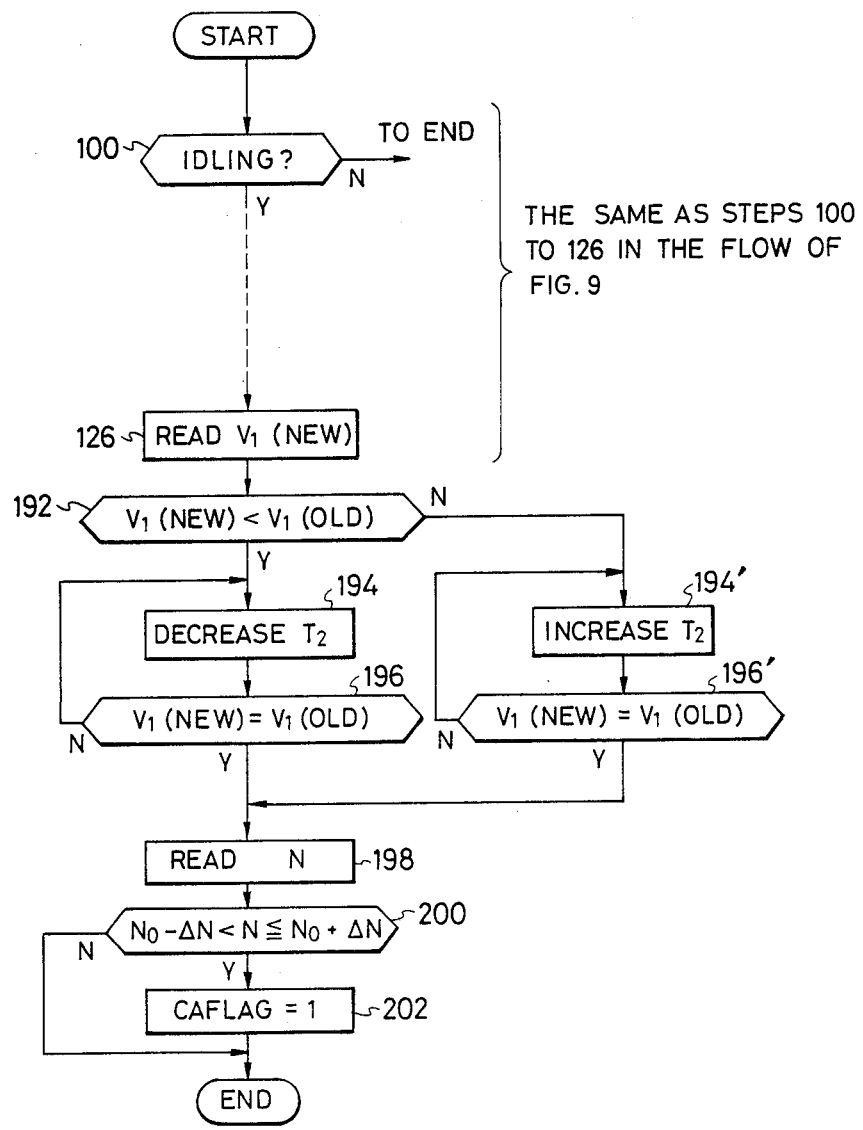
FIG. 15 is a flow chart showing the operation of the another embodiment according to the operational principle explained in FIGS. 13a to 13c and 14.

Next, the explanation will be done of the operation of the embodiment which utilizes the operational principle mentioned above, referring to FIG. 15, which shows a flow chart of the operation.

Since the process from start to the step of reading the output voltage $V_1$ of the oxygen concentration detector is the same as steps 100 to 126 in FIG. 9, detailed steps are omitted in the figure. Further, the output voltage $V_1$ read at the present time is indicated as $V_1(NEW)$, and on the other hand the output voltage $V_1$ read at the previous time is indicated as $V_1(OLD)$. After having read $V_1(NEW)$, it is compared with $V_1(OLD)$ at step 192. If $V_1(OLD)$ is larger than $V_1(NEW)$, the time period $T_2$ of the second mode of operation is decreased until both become equal to each other (steps 194 and 196). The time period $T_2$ when $V_1(NEW)$ has become equal to $V_1(OLD)$ is a time period to be used for the subsequent second mode of operation. On the contrary, when $V_1(OLD)$ is smaller than $V_1(NEW)$, the time period $T_2$ of the second mode of operation is increased until both become equal to each other (steps 194' and 196'). In the same way as mentioned above, the time period $T_2$ when $V_1(NEW)$ has become equal to $V_1(OLD)$ is a time period to be used in the subsequent second mode of operation.

After the time period of the second mode of operation has been thus determined, the number N of revolutions of the engine is read at step 198 and the change in the number of revolutions is checked at step 200. When the change in the number of revolutions is within the predetermined range, at step 202 the value 1 is raised at the flag CAFLAG and the operation ends. If the change in the number of revolutions exceeds the predetermined range, the operation is ended without raising the flag CAFLAG.

According to this embodiment, the operation for rewriting the $\lambda$-table is not necessary and therefore the subsequent process becomes simple.

Figure 12:
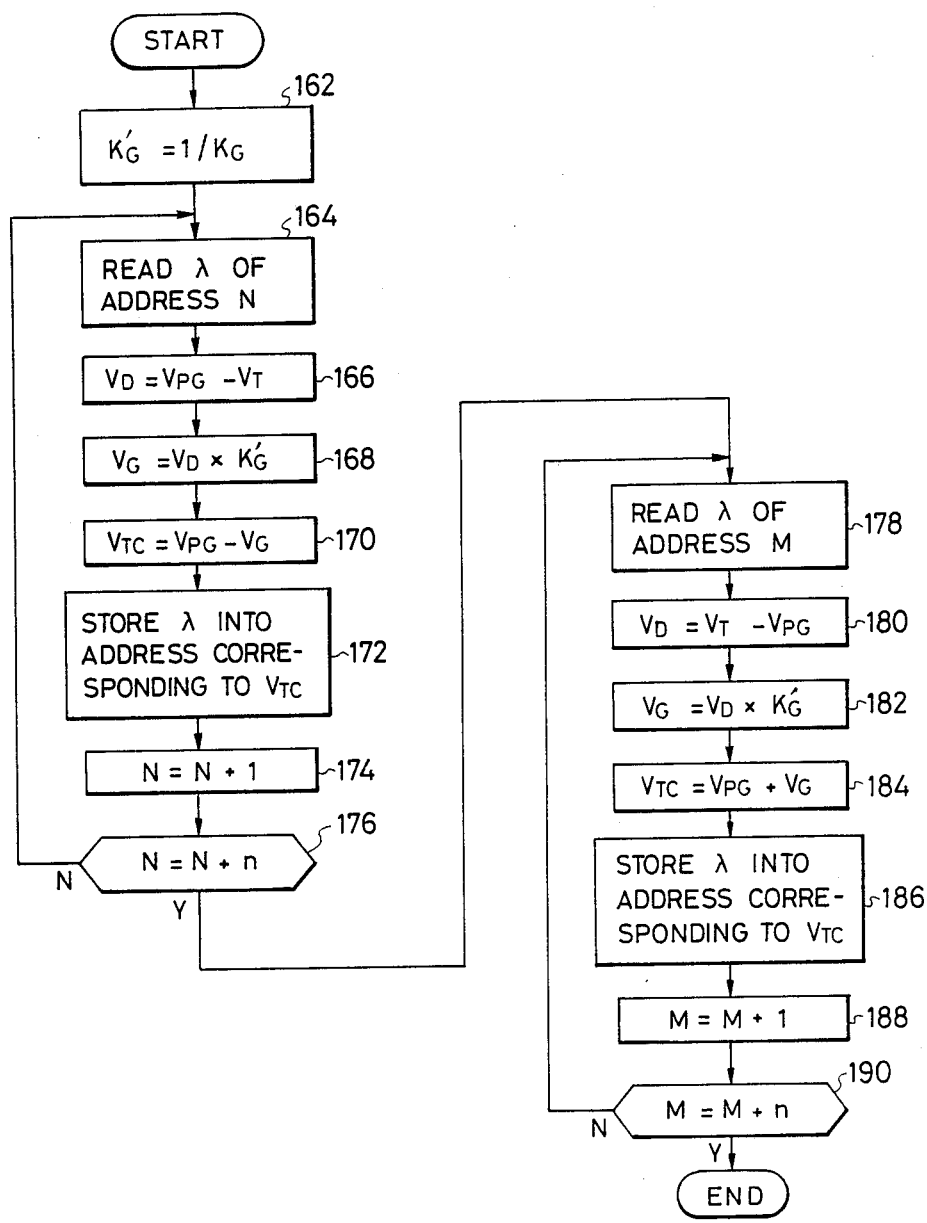
FIG. 12 is a flow chart showig a modification of the correcting operation, in which the contents of the air excess ratio table are rewritten in accordance with the correcting factor $K_G$.

By the way, in the embodiments shown in FIGS. 10 and 12, the correcting factor $K_G$ or its reciprocal value $K_G'$, which are calculated from the old and new gains $K_O$ and $K_N$, has been used in order to specify the correct value of $\lambda$. As apparent from the above mentioned formula (5) for calculating the gain K, the quantity $\Delta Q_a$ of the additional air introduced through the by-pass passage 62 and the quantity $Q_{f0}$ of the injected fuel are included as variables therein. Among the variables of the formula (5), for example, the quantity $\Delta Q_a$ of the additional air can vary for some reason or other after extending over a long period of time. Further, the quantity $Q_{f0}$ of the injected fuel is not always sufficiently accurate, and therefore it is desirable not to use $Q_{f0}$ as a variable for calculating the gain K, if possible. In the following the explanation will be done of an embodiment, in which the correcting factor $K_G$ is obtained without utilizing the quantity $\Delta Q_a$ of the additional air and the quantity $Q_{f0}$ of the injected fuel.

Figure 16:
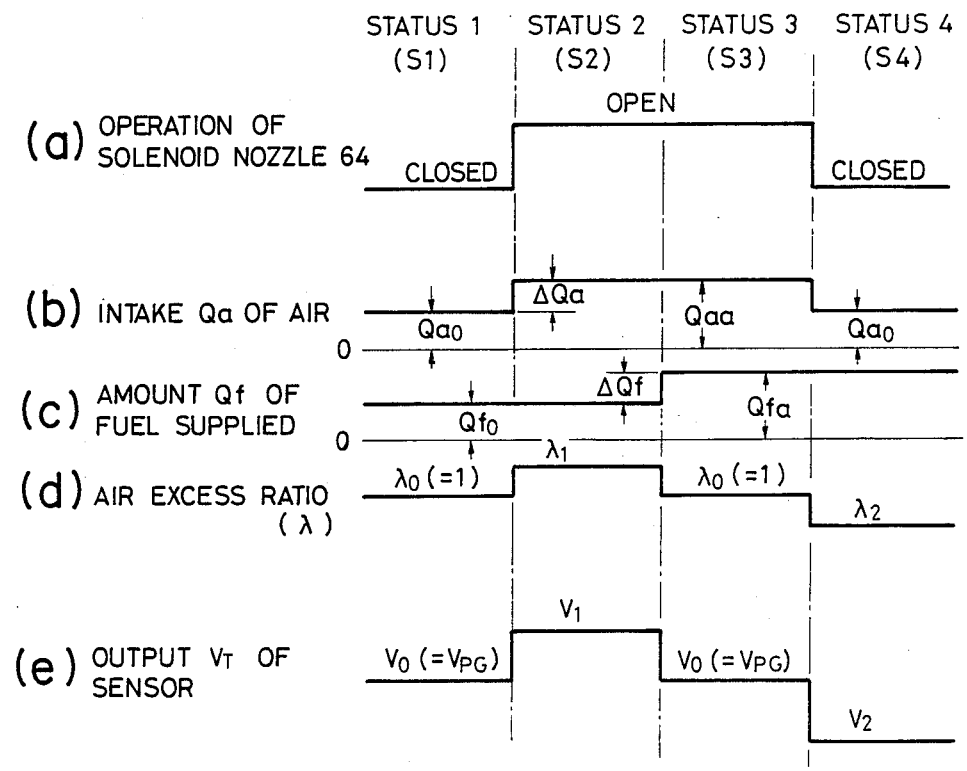
FIGS. 16(a–e) are a diagram for explaining the operational principle of still another embodiment of the present invention.

The operational principle of this embodiment will first of all be explained, referring to FIG. 16, which shows a time chart of the operation of the embodiment.

At first, the engine 52 is brought into the idling condition and the nozzle 64 is closed (cf. FIG. 16(a)). At this time, the quantity $Q_a$ of the air sucked into the engine is $Q_{a0}$ (cf. FIG. 16(b)). Under these conditions, the value of $\lambda$ is made $\lambda_0 (=1.0)$ (cf. FIG. 16(d)). This is accomplished by the feedback control by which the output voltage of the oxygen concentration detector is controlled so as to become $V_0 (=V_{PG})$ (cf. FIG. 16(e)). As a result, the quantity $Q_{f0}$ of the fuel is supplied for the engine (cf. FIG. 16(c)). The operational status of this time is called STATUS 1 (S1).

Next, as the quantity $Q_f$ of the fuel is maintained at $Q_{f0}$ (cf. FIG. 16(c)), the nozzle 64 is opened (cf. FIG. 16(a)) and the amount $\Delta Q_a$ of the additional air is introduced into the engine 52 (cf. FIG. 16(b)). The total quantity $Q_{aa}$ of the air sucked into the engine at this time is expressed as follows.

$$Q_{aa} = Q_{a0} + \Delta Q_a \tag{6}$$

As already described, although the nozzle 64 is opened, the value measured by the airflow meter 56 does not change and corresponds to $Q_{a0}$, because the velocity of the primary air flowing through the throttle valve 58 is equal to the sonic velocity. Therefore, there is also no change in the quantity $Q_{f0}$ of the fuel calculated on the basis of the signal from the airflow meter 56 (cf. FIG. 16(c)). Accordingly, the mixture sucked into the engine 52 becomes lean and the value of $\lambda$ becomes $\lambda_1$ which is larger than $\lambda_0 (=1.0)$ (cf. FIG. 16(d)). The output voltage of the oxygen concentration detector at this time becomes $V_1$, which is larger than $V_0 (=V_{PG})$ (cf. FIG. 16(e)). This operational status is indicated as STATUS 2 (S2) in the figure.

Thereafter, under the condition that the nozzle 64 is opened, the value of $\lambda$ is made $\lambda_0 (=1.0)$ again (cf. FIG. 16(d)). As a result, since the quantity $Q_a$ of the air sucked into the engine 52 is maintained at $Q_{aa}$ (cf. FIG. 16(b)), the quantity of the fuel is increased by $\Delta Q_f$ (cf. FIG. 16(c)). The total quantity $Q_{fa}$ of the fuel to be supplied is expressed as follows.

$$Q_{fa} = Q_{f0} + \Delta Q_f \tag{7}$$

At this time, the output voltage of the oxygen concentration detector becomes $V_0 (=V_{PG})$ (cf. FIG. 16(e)). The operational status of this time is called STATUS 3 (S3).

Thereafter, as the quantity $Q_f$ of the fuel is maintained at $Q_{fa}$ (cf. FIG. 16(c)), the nozzle 64 is closed again (cf. FIG. 16(a)). Thereby the quantity $Q_a$ of the air sucked into the engine 52 returns to $Q_{a0}$ (cf. FIG. 16(b)). The mixture supplied for the engine 52 becomes rich and the value of $\lambda$ becomes $\lambda_2$ which is smaller than $\lambda_0 (=1.0)$ (cf. FIG. 16(d)). The output voltage of the oxygen concentration detector also becomes $V_2$ which is smaller than $V_0 (=V_{PG})$ (cf. FIG. 16(d)). This last operational status is indicated as STATUS 4 (S4) in the figure.

Figure 17:
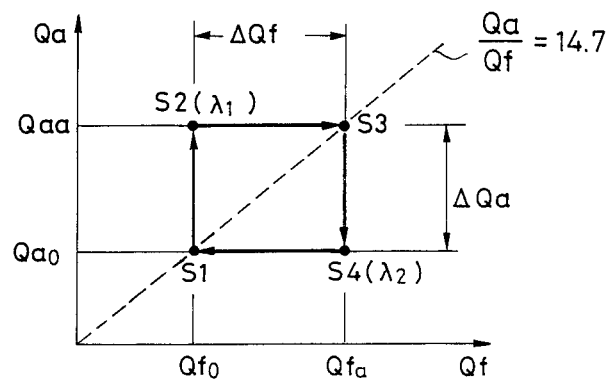
FIGS. 17 and 18 are explanatory drawings of the operation of the still another embodiment.

FIG. 17 is a drawing showing the transition of the above mentioned operational status. In the figure, the abscissa indicates the quantity $Q_f$ of the fuel supplied for the engine 52 and the ordinate the quantity $Q_a$ of the air sucked into the engine 52. A broken line in the figure indicates the line of the stoichiometric A/F ratio ($Q_a/Q_f = 14.7$) of the mixture sucked into the engine 52. Therefore, the operational status of $\lambda = 1.0$ lies on this broken line. The domain over the broken line means that the mixture is lean and the domain under the broken line means that the mixture is rich. The operation mentioned above begins from the point S1 ($Q_{f0}$, $Q_{a0}$) on the broken line. The operational status shifts to the point S2 ($Q_{f0}$, $Q_{aa}$) by opening the nozzle 64 with the quantity $Q_f$ of the fuel maintained at $Q_{f0}$. Then, the quantity $Q_f$ of the fuel is increased by $\Delta Q_f$ with the quantity $Q_a$ of the air maintained at $Q_{aa}$ so that the value of $\lambda$ becomes $\lambda_0$ ($= 1.0$). Thereby the operational status reaches the point S3 ($Q_{fa}$, $Q_{aa}$) on the broken line. Thereafter, the nozzle 64 is closed again. The quantity $Q_a$ of the air is reduced by $\Delta Q_a$ by closure of the nozzle 64, so that the operational status becomes the point S4 ($Q_{fa}$, $Q_{a0}$).

Figure 18:
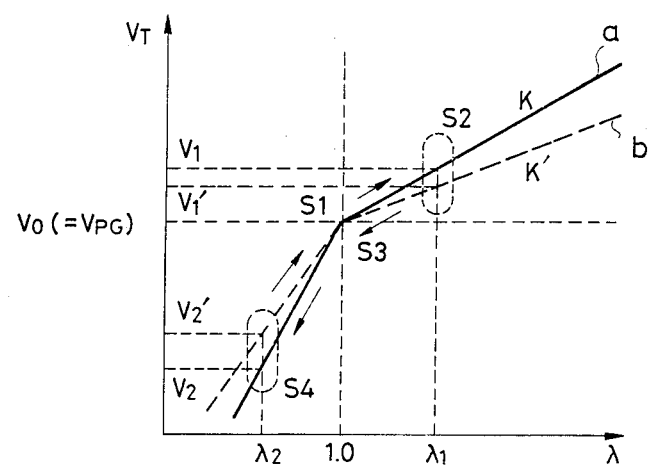

FIG. 18 shows the above mentioned operation on the output characteristic of an oxygen concentration detector. In the figure, a solid line a indicates an initial characteristic before the deterioration of a detector and a broken line b indicates a characteristic of the detector after the deterioration thereof. As an example of the deterioration, here is taken the case, in which the porous layer 6 is choked up. As apparent from the figure, under the statuses S1 and S3, the output voltages of the oxygen concentration detector are the same in both the characteristics and equal to $V_0$ ($=V_{PG}$). Under the statuses S2 and S4, there exists the difference in the output voltage of the detector between the characteristics a and b.

When $\lambda$ is $\lambda_1$, which is larger than 1.0, i.e., in the lean region, the output voltage of the oxygen concentration detector is $V_1$ in the characteristic a, and that becomes $V_1'$ lower than $V_1$ in the characteristic b. On the other hand, when $\lambda$ is $\lambda_2$, which is smaller than 1.0, i.e., in the rich region, the output voltage of the detector is $V_2$ in the characteristic a, and that becomes $V_2'$ higher than $V_2$ in the characteristic b. The change in the output voltage of the detector represents the degree of the aged deterioration and therefore the calibrating operation can be executed on the basis of this change. The method of calibration using the operational principle mentioned above is as follows.

With respect to the characteristic a, the following relation exists between the quantity $Q_a$ of the air and the quantity $Q_f$ of the fuel under the status S1;

$$Q_{a0}/Q_{f0} = C \tag{8}$$

wherein, since $\lambda$ is 1.0, C is equal to 14.7, which corresponds to the stoichiometric A/F ratio.

Under the status S2, since the quantity $\Delta Q_a$ of the air is added, the following relation is established;

$$K(Q_{a0} + \Delta Q_a)/Q_{f0} = V_1 - V_0 \tag{9}$$

wherein K represents the gain of the oxygen concentration detector in the range of $\lambda > 1.0$.

Under the status S3, since $\lambda$ is made 1.0 with the nozzle 64 opened, the following relation is established;

$$(Q_{a0} + \Delta Q_a)/Q_{fa} = C \tag{10}$$

wherein $Q_{fa} = Q_{f0} + \Delta Q_f$.

Under the status S4, the nozzle 64 is closed with the quantity $Q_f$ of the fuel maintained at $Q_{fa}$. Therefore, the following relation is established;

$$\beta K \, Q_{a0}/Q_{fa} = V_0 - V_2 \tag{11}$$

wherein $\beta K$ represents the gain of the oxygen concentration detector in the range of $\lambda < 1.0$.

From the above formulas (8) to (11), the gain K is obtained as follows.

$$K = \frac{1}{C\sqrt{\beta}} \cdot \sqrt{(V_1 - V_0)(V_0 - V_2)} \tag{12}$$

In the same way, the gain $K'$ can be also obtained with respect to the output characteristic b of the oxygen concentration detector which has been deteriorated. The gain $K'$ is expressed by the following formula.

$$K' = \frac{1}{C\sqrt{\beta}} \cdot \sqrt{(V_1' - V_0)(V_0 - V_2')} \tag{13}$$

Accordingly, the correcting factor $K_G$, which is obtained as a ratio of the old and new gains, becomes as follows.

$$K_G = \frac{K'}{K} = \frac{\sqrt{(V_1' - V_0)(V_0 - V_2')}}{\sqrt{(V_1 - V_0)(V_0 - V_2)}} \tag{14}$$

It is of course that the thus obtained correcting factor $K_G$ can be employed for the correcting operation as shown in FIGS. 10 and 12. As apparent from the formula (14), the formula includes only the measured values as variables and therefore the correcting factor $K_G$ can be obtained without being under the influence of the fluctuation of $Q_{a0}$ and $Q_{f0}$ and the opening area of the nozzle 64.

Figure 19:
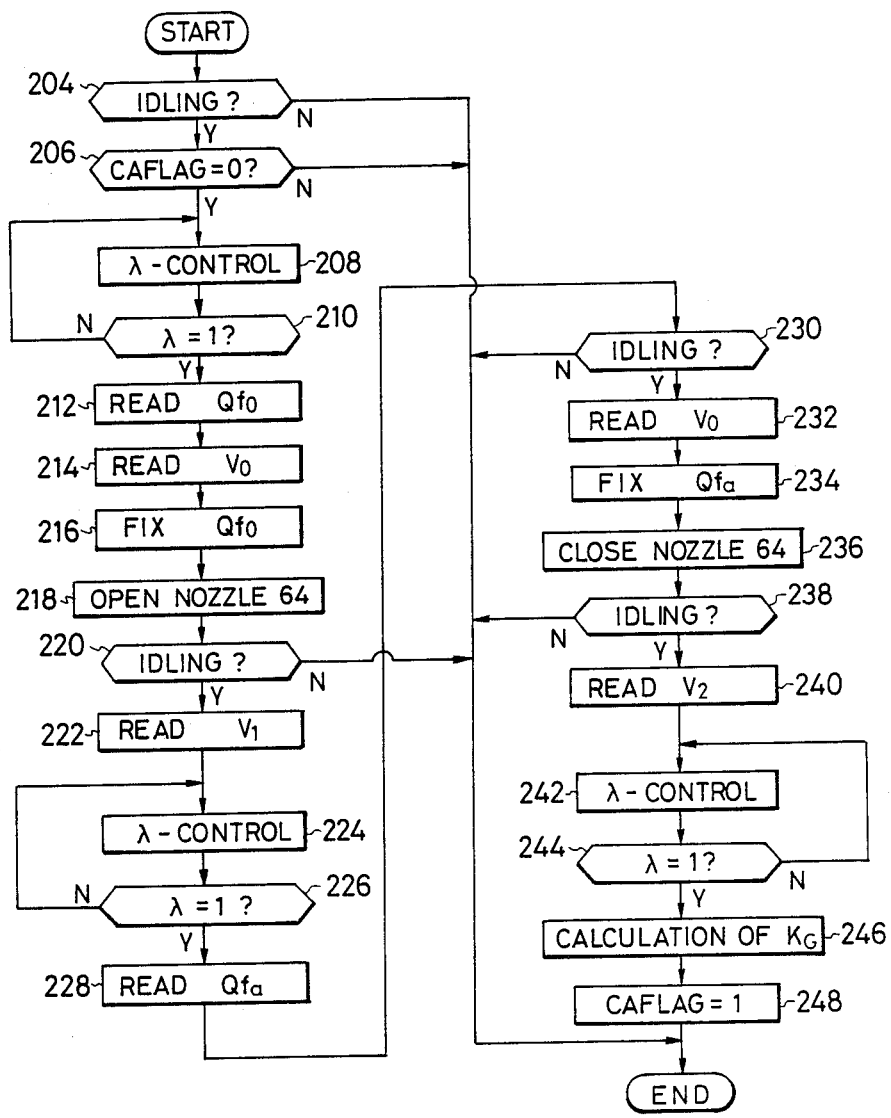
FIG. 19 is a flow chart showing the operation of the still another embodiment according to the operational principle explained in FIG. 16.

Next, the description will be made of the operation by the processing unit 30 according to the above mentioned operational principle. Referring to FIG. 19, there is shown a flow chart of the operation.

At step 204, it is checked whether or not the engine 52 is in the idling condition, and at step 206 the value of the flag CAFLAG is reviewed. If the engine is not in the idling condition or when the value of CAFLAG is 1, the further operation is not executed. If the engine 52 is in the idling condition and the value of CAFLAG is zero, the operation goes to the subsequent step. Namely, the value of $\lambda$ is made 1.0 by executing steps 208 and 210, so that the status S1 is caused. The quantity $Q_{f0}$ of the fuel and the output voltage $V_0$ of the oxygen concentration detector are read at steps 212 and 214, and the quantity $Q_f$ of the fuel is fixed at $Q_{f0}$ at step 216.

At step 218, the nozzle 64 is opened to cause the status S2. After it is confirmed at step 220 that the engine 52 is still in the idling condition, the output voltage $V_1$ of the detector is read at step 222. At this time, if the engine 52 is not in the idling condition, the further operation is not conducted. After having read the output voltage $V_1$, steps 224 and 226 are executed and the value of $\lambda$ is made 1.0 again. Thereby the status S3 is caused. The quantity $Q_{fa}$ of the fuel under the status S3 is read at step 228, and it is again confimed at step 230 that the engine 52 is in the idling condition. When the engine 52 is not in the idling condition, the operation ends. If the engine 52 is in the idling condition, the output voltage $V_0$ of the detector is read at step 232.

Thereafter, at step 234, the quantity $Q_f$ of the fuel is fixed at $Q_{fa}$, which is read at step 228, and the nozzle 64 is closed at step 236. As a result, the status S4 is brought about. Again, it is checked at step 238 whether or not the engine 52 is in the idling condition. When the engine 52 is not in the idling condition, the further operation is not executed. If the engine is still in the idling condition, the output voltage $V_2$ of the detector is read at step 240. By executing subsequent steps 242 and 244, the operational status is returned to the initial status S1. Thereafter, at step 246, the gain K' at the present time is first of all calculated in accordance with the formula (12) on the basis of $V_0$, $V_1$ and $V_2$ read at steps 214, 222, 232 and 240. Then, the gain calculated at the last time or the initial gain K stored in the storage is read out and the correcting factor $K_G$ is calculated by taking the ratio of K and K'. After having calculated the correcting factor $K_G$, the value 1 is raised in the flag CAFLAG at step 248 and the operation ends.

Figure 20:
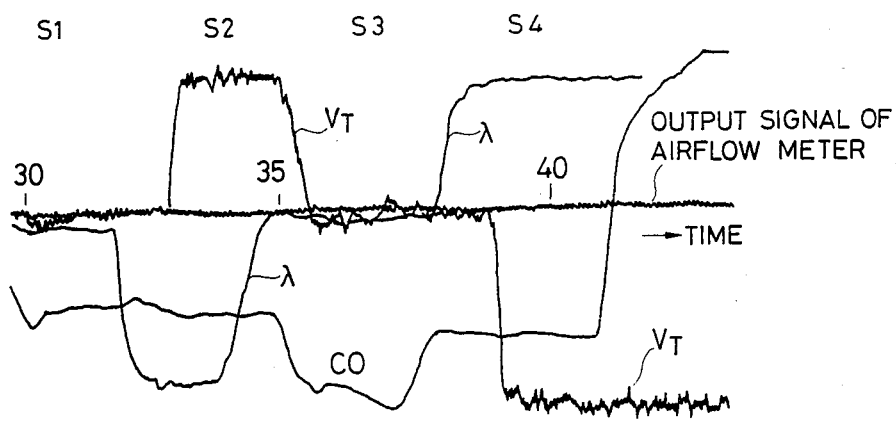
FIGS. 20 and 21 show an example of the experimental result of the present invention.
Figure 21:
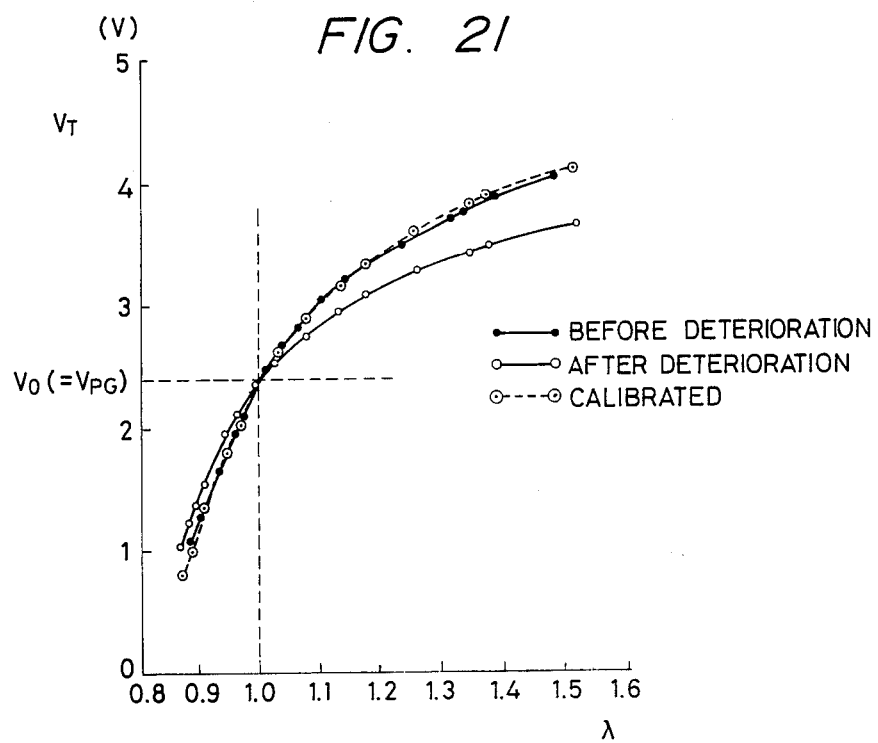

The result of an experiment, in which the present invention is applied to an actual internal combustion engine, is shown in FIG. 20. As will be understood from the figure, the air excess ratio $\lambda$ and the output voltage $V_T$ of the oxygen concentration detector varies in accordance with the operational status; however the output signal of the airflow meter 56, as described above, does not change at all, because the velocity of the air flowing therethrough is equal to the sonic velocity. FIG. 21 shows the comparison among an output characteristic of an oxygen concentration detector before the deterioration thereof (i.e., an initial output characteristic), an output characteristic of the oxygen concentration detector after the deterioration thereof and a calibrated characteristic. The calibrated one has been obtained by correcting the characteristic after the deterioration by the correcting factor calculated on the basis of the actual output values of the oxygen concentration detector in the operation shown in FIG. 20. It will be apparent from this comparison that the calibrated characteristic well coincides with the output characteristic before the deterioration, i.e., the initial output characteristic. The difference between both the characteristics is 1 to 2% in terms of the A/F ratio.

Through the above described embodiments, the calibrating operation has been conducted in the idling condition of the engine. However, the timing of the calibrating operation is not limited to the time of the idling of the engine. Whenever the engine operates in the steady state, the calibrating operation can be conducted.

As described above, in the A/F ratio sensor according to the present invention, the error in the measurement of the A/F ratio caused by the aged deterioration of the oxygen concentration detector can be corrected easily and accurately, so that the accurate engine control is made possible.

Since certain changes may be made in the above apparatus and processes without departing from the scope of the invention herein involved, it is intended that all matter contained in the above description or shown in the accompanying drawings shall be interpreted in an illustrative and not in a limiting sense.

We claim:

1. An apparatus for detecting an air/fuel ratio of mixture supplied for an internal combustion engine, which is provided with means for detecting the concentration of residual oxygen remaining in exhaust gas of the engine and determines the air/fuel ratio by retrieving an air excess ratio table prepared in advance with an output value of the concentration detecting means, characterized by:

means for introducing a predetermined quantity of additional air into the engine, in addition to primary air sucked into the engine through an airflow meter and a throttle valve, and a processing unit for controlling said introducing means to introduce the additional air into the engine for a predetermined period during the steady condition of operation of the engine and processing output signals, which are produced before and after introduction of the additional air, to determine the air/fuel ratio on the basis of the processing result.

2. An apparatus for detecting an air/fuel ratio as defined in claim 1, wherein the additional air is introduced into the engine under the condition that the flowing velocity of the primary air is substantially equal to the sonic velocity.

3. An apparatus for detecting an air/fuel ratio as defined in claim 1, wherein said introducing means comprises a by-pass passage bridging the airflow meter and the throttle valve and a nozzle which controls the communication of air flowing therethrough in response to a control signal from said processing unit.

4. An apparatus for detecting an air/fuel ratio as defined in claim 1, wherein the additional air is introduced into the engine by further opening the throttle valve by a small amount of angle from the present opening angle thereof for a certain period of time.

5. An apparatus for detecting an air/fuel ratio as defined in claim 1, wherein an output value produced by the concentration detecting means during the usual operation thereof is corrected in accordance with the processing result and the air excess ratio table is retrieved with the corrected output value.

6. An apparatus for detecting an air/fuel ratio as defined in claim 1, wherein the contents of the air excess ratio table are rewritten in accordance with the processing result every time the processing process is executed and the air excess ratio table is directly retrieved with the output value of the concentration detecting means during the usual operation thereof.

7. An apparatus for detecting an air/fuel ratio as defined in claim 1, wherein during a processing process said processing unit:

in a first step adjusts an air/fuel ratio of the mixture supplied for the engine to substantially the stoichiometric value, in a second step reads the quantity of fuel being supplied for the engine and a first current output value of the concentration detecting means, in a third step fixes the quantity of the fuel at the value read at the second step and introduces the additional air into the engine, in a fourth step reads a second current output value of the concentration detecting means, in a fifth step calculates a gain of the concentration detecting means on the basis of the first and second current output values read at the second and fourth steps and compares the calculated gain with a previously calculated gain to obtain a correcting factor, for determination of the air/fiel ratio.

8. An apparatus for detecting an air/fuel ratio as defined in claim 7, wherein, at latest before the fifth step, in an intermediate step, said processing unit confirms that the change in the number of revolutions of the engine remains within a predetermined range and stops the execution of further steps of said processing process if the change in the number of revolutions exceeds the predetermined range.

9. An apparatus for detecting an air/fuel ratio as defined in claim 7, wherein said processing unit executes the fourth step after a certain period of time from introduction of the additional air.

10. An apparatus for detecting an air/fuel ratio as defined in claim 7, wherein an output value produced by the concentration detecting means during the usual operation thereof is corrected by said concentration detecting means in accordance with the correcting factor and the air excess ratio table is retrieved with the corrected output value.

11. An apparatus for detecting an air/fuel ratio as defined in claim 7, wherein said concentration detecting means rewrites the contents of the air excess ratio table in accordance with the correcting factor every time the processing process is executed and directly retrieves the air excess ratio table with an output value of the concentration detecting means.

12. An apparatus for detecting an air/fuel ratio as defined in claim 1, wherein during a processing process said processing unit:

in a first step adjusts an air/fuel ratio of the mixture supplied for the engine to substantially the stoichiometric value, in a second step reads the quantity of fuel being supplied for the engine and a first current output value of the concentration detecting means, in a third step fixes the quantity of the fuel at the value read at the second step and thereafter introduces the additional air into the engine, in a fourth step reads a second current output value of the concentration detecting means, in a fifth step calculates the air/fuel ratio of the mixture supplied for the engine to substantially the stoichiometric value, in a sixth step reads the quantity of the fuel and a third current output value of the concentration detecting means, in a seventh step fixes the quantity of the fuel at the value read at the sixth step and thereafter stops introduction of the additional air, in a eighth step reads a fourth current output value of the concentration detecting means, in a ninth step calculates a gain of the concentration detecting means on the basis of the first, second, third and fourth current output values respectively read at the second, fourth, sixth and eighth steps and compares the gain calculated with a gain previously calculated in the same manner and stored to obtain a correcting factor, for determination of the air/fuel ratio.

13. An apparatus for detecting an air/fuel ratio as defined in claim 12, wherein, before reading the output values of the concentration detecting means, said processing unit confirms that the change in the number of revolutions of the engine remains within a predetermined range and stops the execution of further steps of said processing process if the change in the number of revolutions of the engine exceeds the predetermined range.

14. An apparatus for detecting an air/fuel ratio as defined in claim 12, wherein an output value produced by the concentration detecting means during the usual operation thereof is corrected by said concentration detecting means in accordance with the correcting factor and the air excess ratio table is retrieved with the corrected output value.

15. An apparatus for detecting an air/fuel ratio as defined in claim 12, wherein said concentration detecting means rewrites the contents of the air excess ratio table in accordance with the correcting factor every time the processing process is executed and directly retrieves the air excess ratio table with an output value of the concentration detecting means.

16. An apparatus for detecting an air/fuel ratio as defined in claim 1, wherein a gain of the concentration detecting means is so adjusted that the output value of the concentration detecting means upon introduction of the additional air becomes equal to an output value of the concentration detecting means which has been read and stored upon introduction of the additional air of the previous time.

* * * * *